US005292661A

United States Patent [19]

Cole et al.

[11] Patent Number: 5,292,661

[45] Date of Patent: Mar. 8, 1994

[54] NON-AFLATOXIGENIC ASPERGILLUS PARASITICUS STRAINS AND THEIR USE IN CONTROLLING AFLATOXIN CONTAMINATION

[75] Inventors: Richard J. Cole; Joe W. Dorner, both of Albany; Paul D. Blankenship, Preston, all of Ga.

[73] Assignee: The United States of America as represented by the Secretary of Agriculture, Washington, D.C.

[21] Appl. No.: 741,691

[22] Filed: Aug. 7, 1991

[51] Int. Cl.[5] .......................... C12N 1/14; C07G 17/00; A01N 63/00; A01N 25/32

[52] U.S. Cl. .................................. 435/267; 435/256.1; 424/93 Q; 424/405; 424/406

[58] Field of Search ............. 435/267, 254; 424/93 Q, 424/405, 406

[56] References Cited

U.S. PATENT DOCUMENTS

| | | | |
|---|---|---|---|
| 4,931,398 | 6/1990 | Kimura | 435/252.5 |
| 5,049,498 | 9/1991 | Spivack et al. | 435/254 |

OTHER PUBLICATIONS

Cole, R. J., et al., *Dev. Ind. Microbiol.*, vol. 23, pp. 229-236 (1982).

Cole, R. J., et al., Aflatoxin Contamination of Groundnut: Proceedings of the International Workshop, Oct. 6-9, 1987, ICRISAT Center, India.

Ehrlich, et al., *Experientia*, vol. 41, pp. 691-693 (1985).

Wicklow, et al., *Phytopathology*, vol. 70, pp. 761-764 (1980).

Dorner, J. W., et al., *Mycopathologia*, vol. 87, pp. 13-15 (1984).

Cole, R. J., et al., *Appl. Environ. Microbiol.*, vol. 52, pp. 1128-1131 (1986).

Bennett, J. W. and L. A. Goldblatt, *Sabouraudia*, vol. 11, pp. 235-241 (1973).

*Primary Examiner*—Douglas W. Robinson
*Assistant Examiner*—Deborah K. Ware
*Attorney, Agent, or Firm*—M. Howard Silverstein; John D. Fado; Joseph A. Lipovsky

[57] ABSTRACT

A process for biologically controlling the preharvest accumulation of aflatoxin in soil-borne crops. Non-aflatoxigenic strains of *Aspergillus parasiticus* having all of the relevant identifying characteristics of NRRL 18786 and NRRL 18991 are shown to inhibit aflatoxin production by native toxigenic strains of *Aspergillus flavus* or *Aspergillus parasiticus* in the soil environment.

5 Claims, No Drawings

NON-AFLATOXIGENIC ASPERGILLUS PARASITICUS STRAINS AND THEIR USE IN CONTROLLING AFLATOXIN CONTAMINATION

BACKGROUND OF THE INVENTION

1. Field of the Invention

This invention relates to a method for the preharvest control of aflatoxin in crops. This is accomplished by inoculating either the crop or the soil in which it is grown with non-aflatoxigenic strains of *Aspergillus parasiticus* (*A. parasiticus*), deposited and designated as NRRL 18786 and NRRL 18991.

2. Description of the Prior Art

Aflatoxins are potent hepatotoxic, carcinogenic compounds produced by fungi, particularly *Aspergillus flavus* (*A. flavus*) and *A. parasiticus* [Cast, (1989) Mycotoxins: economic and health risks. Report 116. Council for Agricultural Science and Technology). When these fungi invade and grow in agricultural commodities such as peanuts, corn, and cottonseed, the resulting contamination with the aflatoxins often makes the commodity unfit for consumption. They are a serious threat to humans and animals [Cast, Counc. Agric. Sci. Technol. Rep., Vol. 80, (1979), Ames, IA., 56 pp.]. The four naturally-occurring aflatoxins are designated $B_1$,$B_2$,$G_1$, and $G_2$ and will hereafter be collectively referred to as aflatoxin.

The United States peanut industry has identified aflatoxin contamination of peanuts as the number one problem for which a solution is needed [Consensus Report of the National Peanut Council Quality Task Force (1987) National Peanut Council].

Because peanuts are used primarily for food, strict regulatory limits for the amount of aflatoxin allowable in finished peanut products have been established. Although the U.S. Food and Drug Administration (FDA) has an action level of 20 parts per billion (ppb) of total aflatoxins in finished products, several states are considering much stricter limits for aflatoxin in food. For this reason the U.S. peanut industry has a goal to ensure the delivery of aflatoxin-free peanut products by the year 2000.

Although aflatoxin contamination of peanuts can occur during postharvest curing and storage, the most significant source of contamination is usually preharvest contamination, which occurs during periods of late-season drought stress as peanuts are maturing. The only known method for controlling preharvest aflatoxin contamination in peanuts is irrigation [Cole, R. J. (1982), Dev. Ind. Microbiol. Vol. 23, pp. 229-236; Cole, R. J., Aflatoxin Contamination of Groundnut: Proceedings of the International Workshop, Oct. 6-9, 1987, ICRISAT Center, India], an option that is unavailable to the majority of peanut growers.

It has previously been found that co-cultivation of either *A. parasiticus* or *A. flavus* with species of Penicillia reduce levels of aflatoxin production while co-cultivation with Fusaria had no such effect [Ehrlich, et al., Experientia, Vol. 41, pp. 691-693, (1985)]. These tests did not involve the use of a soil environment. Co-cultivation with *A. niger* completely eliminated the production of aflatoxin by a producer culture of *A. flavus* [Wicklow, et al., Phytopathology, Vol. 70, pp. 761-764, (1980)]. This testing was done under laboratory controlled conditions in which the food source involved sterilized corn kernels.

SUMMARY OF THE INVENTION

It has now been discovered that a known strain of *Aspergillus parasiticus* (NRRL 18991) is non-aflatoxigenic and competes with native toxigenic strains of *A. parasiticus* and *A. flavus* under field conditions, causing a reduction in aflatoxin production and subsequent crop contamination. It has further been discovered that a non-aflatoxigenic mutant (NRRL 18786) selected following UV mutagenesis of *Aspergillus parasiticus* NRRL 18991, unlike its parent, fails to produce O-methylsterigmatocystin (OMS) which is mutagenic and potentially carcinogenic; yet still retains the ability to reduce the aflatoxin production of native strains through biocompetition.

In accordance with this discovery, it is an object of the invention to biologically control the preharvest accumulation of aflatoxin in soil-borne crops.

A further object of the invention is to define a novel mutant species of Aspergillus which is non-toxigenic.

Other objects and advantages of this invention will become readily apparent from the ensuing description.

DETAILED DESCRIPTION OF THE INVENTION

The underlying theory of the instant invention is that addition of a highly competitive, non-toxigenic strain of *A. parasiticus* (biocompetitive agent) to soil would result in lower concentrations of aflatoxin in peanuts. The rationale is that the biocompetitive agent would dominate the soil microflora and prevent the buildup of aflatoxin-producing strains of *A. flavus/parasiticus* that normally occurs during late-season drought. Through biological competition, the toxigenic strains found naturally in soil would be replaced by a non-toxigenic strain added to the soil. Therefore, peanuts subjected to late-season drought stress would be invaded predominately by the biocompetitive agent, which is unable to produce aflatoxin. The fungi useful in the instant invention are strains possessing the identifying characteristics of *A. parasiticus* (NRRL 18991 and NRRL 18786). *A. parasiticus* NRRL 18991 isolated from the environmental control plots at the National Peanut Research Laboratory (NPRL) in 1980 and subsequently shown not to produce aflatoxin [Dorner, J. W. (1984), Mycopathologia, Vol. 87, pp. 13-15]. At that time, it was the only naturally-occurring strain of *A. parasiticus* known that did not produce aflatoxin. This particular strain was selected for use in the instant invention because it met several heretofore unrecognized criteria. First, for an organism to be successful as a biocompetitive agent for aflatoxin control, it should occupy the same ecological niche as *A. flavus/parasiticus* and compete with the native strains under the environmental conditions that lead to aflatoxin contamination; i.e., hot, dry peanut soil during periods of late-season drought stress. Second, it was found to be a stable, non-producer of aflatoxin. Third, *A. parasiticus* was shown to be more persistent in soil than *A. flavus*. [Cole, R. J. (1986), Appl. Environ. Microbiol. Vol. 52, pp. 1128-1131]. Fourth, this particular strain was a prolific producer of sclerotia, which enhances its survivability and competitiveness in the soil. Although this strain (NRRL 18991) does not produce aflatoxin, it does produce O-methylsterigmatocystin (OMS), the immediate biosynthetic precursor to aflatoxin $B_1$. This fact provided the use of OMS as a chemical marker to monitor the activity of the fungus in the soil and in peanuts.

The fact that *A. parasiticus* (NRRL 18991) accumulates OMS could make it unacceptable as a general-use biocompetitive agent because OMS is mutagenic and possesses the dihydrobisfuran moiety reportedly responsible for aflatoxin's carciogenicity [Cast (1989). Mycotoxins: economic and health risks. Report 116. Council for Agricultural Science and Technology, 91 pp.]. Because of these potential drawbacks, a UV-induced mutant of the NRRL 18991 strain was developed by growing cultures of the parent strain which were irradiated under short wave UV light by the method of Bennett and Goldblatt [Bennett, J. W. and L. A. Goldblatt (1973), Sabouraudia, Vol. 11, pp. 235-241]. Surviving colonies were isolated, grown on potato dextrose agar (PDA) slants and analyzed for OMS and aflatoxin by adding 3 mL chloroform to the slant tube, vortexing for one minute, and filtering through microfiber filter paper. The filtrate was evaporated to dryness under nitrogen, redissolved in 50 μL chloroform, and mixed. A 2 μL aliquot was spotted on a silica gel 60 thin-layer chromatography (TLC) plate along with standards of aflatoxin and OMS, and plates were developed in a solvent system of chloroform-acetone (93-7, v/v). Developed plates were viewed under long-wave ultraviolet light before and after spraying with 50% ethanolic sulfuric acid. Aflatoxins were visualized as bluish or greenish fluorescent spots before spraying and as yellowish spots following spraying. OMS was a blue fluorescent spot before spraying and an intensely yellow fluorescent spot after spraying. An acceptable mutant identified as M52 (NRRL 18786) was subsequently found. NRRL 18786 accumulates versicolorin A, another intermediate in aflatoxin biosynthesis without producing detectable amounts of OMS.

A series of tests were carried out to determine the utility of the instant disclosed strains in reducing aflatoxin contamination of soil-borne crops. The following examples are intended only to further illustrate the invention and are not intended to limit its scope which is defined by the claims.

TEST PROCEDURE

Soil Microflora Analysis

The relative number of colony forming units (CFU) of aflatoxin-producing strains of *A. flavus/parasiticus* and the biocompetitive agents in treated and nontreated soils were determined at various times. Five soil samples of approximately 250 g were taken to a depth of 5 cm at various locations in the plots. Each sample was well mixed and screened through a 20 mesh sieve. Fifteen g of screened soil was then added to 300 mL of a sterile 0.2% agar solution in a 500 mL Erlenmeyer flask. After swirling, 10 0.5 mL portions (equivalent to 0.025 g of soil) were placed in the middle of petri plates containing 20 mL of the following selective medium: 20 g agar; 10 g glucose; 5 g peptone; 30 g NaCl; 1 g $K_2HPO_4$; 0.5 g $MgSO_4$; 6 mL of a botran solution (90 mL acetone, 30 mg botran); 5 mL of an antibiotic solution (20 mL water, 0.2g chlortetracycline HCl, 0.2 g streptomycin sulfate); 1 L distilled water (David M. Wilson, personal communication). A glass rod was placed on the agar as the plate was rotated to distribute the soil suspension over the surface of the agar. For samples with colonies too numerous to count, appropriate dilutions of the soil suspension were made and samples were replated. Plates were incubated for four days at 30° C. and *A. flavus/parasiticus* colonies were counted. CFU of these fungi per gram of soil were determined by multiplying the average number of colonies per plate by 40.

The *A. flavus/parasiticus* colonies were then tested to determine the percentage that were aflatoxin producers, one of the biocompetitive agents, or neither. Approximately 10% of the total colonies were randomly chosen and transferred to PDA slants and incubated at 30° C. for 7 days. Each slant was analyzed for aflatoxin and the chemical markers, OMS and versicolorin A, as described for the analysis of slants of mutated colonies. The resulting percentages were then multiplied by the total CFU per gram to determine the actual CFU per gram of each type.

EXAMPLE 1

First Crop Growing Season

Six rows, spaced 0.9 m apart, of cv. Florunner peanuts were grown in an environmental control plot (5.5 m×12.2 m) at the NpRL, Which provided the late-season drought and soil temperature conditions that were previously determined to be optimum for preharvest aflatoxin contamination of peanuts. Cultural practices recommended by the Georgia Cooperative Extension Service were used until 100 days after planting (DAP), at which time the peanuts received a final irrigation. The stress period was started at 107 DAP.

The biocompetitive agent (*A. parasiticus,* NRRL 18991) was grown in six 2.8 L Fernbach flasks on liquid YES medium (15% sucrose; 5% mycological broth, pH 4.8; 2% yeast extract) for 2 weeks at 27° C. The cultures were combined and homogenized in 15 L of water plus 0.05% Tween 20 with an Ultra-Turrax homogenizer. The homogenate was strained through cheesecloth and applied over three of the six rows of peanuts at 32 DAP using a garden sprinkler. A similar application was made 100 DAP, the day of the final irrigation. Each of the treated and nontreated rows was divided into sections so that four random samples of each were harvested after 23, 30, 37, and 44 days of stress. Samples were shelled with a Federal State Inspection Service sample sheller and sized into commercial size categories (jumbo, medium, number 1, other-edible, and oil stock). Damaged and visibly molded kernels were removed from each category and combined as a single category.

Jumbo, medium, number 1, and other-edible size peanuts were prepared for analysis by grinding to pass a 20 mesh sieve. Aflatoxin analyses of each category were carried out on 75% of the ground samples using the high performance liquid chromatography (HPLC) method of Dorner and Cole. All oil stock and damaged peanuts were analyzed for aflatoxin only. The remaining 25% of the ground was analyzed for OMS with an HPLC method developed for this study. The ground peanut samples were extracted with chloroform, filtered through microfiber filter paper, evaporated to an oil on a rotary evaporator, and applied to a Florisil Sep PAK (Waters Chromatography Division, Millipore Corp., Milford, Mass. 01757) in cyclohexane. The Sep PAK was washed with 10 mL volumes of cyclohexane, cyclohexane-ethyl acetate (60-40, v/v), and OMS was eluted with 10 mL of ethyl acetate. The ethyl acetate fraction was evaporated to dryness and redissolved in 1 mL of ethyl acetate-hexane (85-15, v/v). Fifty μL was injected into an HPLC system consisting of a waters silica cartridge (5 mm×10 cm) in a radial compression module, eluted with a mobile phase of ethyl acetate-hexane (85-15, v/v), and detected at 310 nm with a Waters model 490E programmable UV detector. Quantitation was achieved with a Waters model 730 data module which compared peak areas of samples to areas of OMS standard solutions.

Results of the First Crop Growing Season

Results of aflatoxin and OMS analyses are presented in Table 1. By 23 stress days, aflatoxin concentrations were already high in the inedible peanuts (other-edible, oil stock, and damaged peanuts). Aflatoxin has been shown consistently to appear first and achieve higher concentrations in these high risk categories. Therefore, in milling and processing operations, these peanuts are removed from peanuts destined for edible use, regardless of aflatoxin concentration. Aflatoxin concentrations were unacceptably high in both treated and untreated edible peanuts (jumbo, medium, and number 1) from the 30 stress-day sampling. However, as the stress period continued aflatoxin concentrations decreased in edible peanuts from soil that was treated with the biocompetitive agent to a level that is under the action level set by the FDA. On the other hand, aflatoxin concentrations continued to increase during the stress period in edible peanuts grown in soil that was not treated with the biocompetitive agent. Results of OMS analyses indicated that the biocompetitive agent was actively contaminating peanuts, but it had not excluded all wild, aflatoxigenic strains of *A. flavus/parasiticus.*

EXAMPLE 2

Second Crop Growing Season

Because of the positive results of the first crop growing season, the study was continued for a second crop growing season with several modifications. Preplant soil microflora analysis indicated that a large population of the biocompetitive agent remained in the soil from the previous year's study, including the area that was not treated with the biocompetitive agent in the first crop growing season. Therefore, soil was removed from one-half of the plot to a depth of 1 m and replaced with new soil. A barrier was placed between the two halves of the plot, and the half containing the new soil served as a nontreated control while the half with the old soil was used to determine the effectiveness of the biocompetitive agent for the second crop growing season. No additional biocompetitive agent was added to the soil.

Florunner peanuts were grown and subjected to late-season drought stress as in the previous year. The final irrigation was applied 98 DAP, the stress period started 105 DAP, and all peanuts were harvested 154 DAP after 49 days of stress. All peanuts from treated soil were analyzed for aflatoxin and OMS as in the first crop growing season, but only edible peanuts grown in the new soil were analyzed for aflatoxin.

In addition to the preplant soil microflora analysis, soil samples were also taken at harvest to compare propagule levels of the biocompetitive agent and wild strains of *A. flavus/parasiticus* with those determined prior to planting.

Results of the Second Crop Growing Season

Results of the preplant and harvest soil microflora analyses are presented in Table 2. Populations of both aflatoxin-producing strains of *A. flavus/parasiticus* and the biocompetitive agent approximately doubled during the season. However, the population of the biocompetitive agent far outweighed that of wild-type aflatoxin producers. The final population of the biocompetitive agent was comparable to levels commonly seen for *A. flavus/parasiticus* in peanut soils exposed to late-season drought stress (unpublished data). This demonstrated that a high degree of replacement of toxigenic strains of *A. flavus/parasiticus* by the biocompetitive agent occurred.

TABLE 1

Aflatoxin and O-methylsterigmatocystin (OMS) concentrations (ppb) in peanuts from soil treated and not treated with the biocompetitive agent in the first crop growing season.

| Stress Period (days) | Treatment | Aflatoxin Edible[1] | Aflatoxin Inedible[2] | OMS Edible |
|---|---|---|---|---|
| 23 | Treated | 4 | 577 | 15 |
| | Untreated | 1 | 739 | 7 |
| 30 | Treated | 222 | 2,534 | 31 |
| | Untreated | 97 | 4,775 | 41 |
| 37 | Treated | 19 | 11,783 | 120 |
| | Untreated | 106 | 12,688 | 5 |
| 44 | Treated | 11 | 7,035 | 94 |
| | Untreated | 531 | 21,692 | 81 |

[1]Values are the weighted average for jumbo, medium, and number 1 sizes.
[2]Values are the weighted average for the other-edible, oil stock, and damaged categories.

TABLE 2

Soil populations (CFU per gram) of aflatoxigenic strains of *A. flavus/parasiticus* and biocompetitive agent prior to planting and at harvest for the second crop growing season treated soil.

| Sampling | *A. flavus/parasiticus* | Biocompetitive Agent |
|---|---|---|
| Preplant | 207 | 5,233 |
| Harvest | 442 | 10,925 |

Aflatoxin concentration in edible, treated peanuts in the second crop growing season were by far the lowest ever observed during nine years of research using the environmental control plots (Table 3). Together, edible peanuts contained only 1 ppb of aflatoxin compared to 96 ppb in edible peanuts from untreated soil. By comparison, the OMS concentration in edible peanuts from treated soil was 172 ppb, providing strong evidence that the biocompetitive agent had invaded peanuts and proliferated to a far greater extent than aflatoxigenic strains. The inedible peanuts still had significant amounts of aflatoxin, but these too were much lower than had been observed in previous crop growing seasons and were much lower than the amounts of OMS present.

TABLE 3

Second crop growing season aflatoxin and OMS concentrations (ppb) in peanuts from soil treated in the first crop growing season with the biocompetitive agent and new, untreated soil. All peanuts were subjected to 49 days of drought stress.

| Category | Aflatoxin | OMS |
|---|---|---|
| Treated Soil | | |
| Jumbo | 0 | 45 |
| Medium | 0 | 238 |
| Number 1 | 4 | 98 |
| Edible weighted average | 1 | 172 |
| Other-edible | 0 | 1,288 |
| Oil stock | 68 | 1,776 |
| Damage | 3,908 | 13,311 |
| Inedible weighted average | 515 | 2,945 |
| Untreated Soil | | N/A* |
| Edible | 96 | |

*Peanuts from untreated soil were not analyzed for OMS.

EXAMPLE 3

Third Crop Growing Season

The study of the second crop growing season was essentially repeated. Soil was again replaced in the untreated half of the plot and no additional biocompetitive agent was added to the treated half. This soil was last inoculated with the biocompetitive agent at the start of the first crop growing season.

Additional studies were conducted to determine the effectiveness of the M52 mutant from *A. parasiticus* NRRL 18991 as a biocompetitive agent. Four environmental control plots (5.5 m×6 m) were inoculated with two different inoculum levels of the mutant in order to begin determining the effect of inoculum level on fungal soil populations and aflatoxin contamination. To determine the number of CFU in a Fernbach flask after homogenization with water and 0.05% Tween 20, serial dilutions of three flasks were plated and the average determined to be approximately $120\times10^9$ CFU per flask. Therefore, it was decided to broadcast the homogenized and cheesecloth-strained contents of five Fernbach flasks ($600\times10^9$ CFU) over each of two plots to serve as the high inoculum treatments. Half the contents of one flask ($60\times10^9$ CFU) were broadcast over each of the other two plots to serve as low inoculum treatments. These plots were inoculated 57 days before peanuts were planted. The day following inoculation these plots were irrigated with 4 cm of water.

Peanuts for this and the continuing study were grown as in previous years with final irrigation occurring 92 DAP, stress period beginning 99 DAP, and harvesting 147 DAP (48 days of stress).

All peanuts were harvested and handled as previously described, except that all peanuts were analyzed for aflatoxin only. Soil samples for microflora analysis were collected from all plots on the day after planting, 99 DAP (beginning of stress period), and on the day of harvest.

Results of the Third Crop Growing Season

Results of soil microflora analyses conducted during the third crop growing season appear in Table 4. As previously observed in new soil, wild strains of *A. flavus/parasiticus* were relatively low prior to planting (40 propagules per gram) and increased dramatically by harvest time (4386 ppg.). In the continuing study, populations of aflatoxin producers and the biocompetitive agent remained fairly constant, indicating that this soil could not support a significant buildup of either type. In comparing the populations at harvest of the untreated soil with those of the soil from the continuing study, it is interesting that the wild *A. flavus* propagules and biocompetitive agent propagules were essentially reversed in the two treatments. This shows that introduction of a relatively large fungal population did not result in a final population that was higher than that of wild strains of *A. flavus/parasiticus* under these conditions.

TABLE 4

Fungal soil populations (CFU per gram) from the third crop growing season sampled prior to planting, 97 days after planting (DAP), and at harvest.

| Treatment | Preplant | | 97 DAP | | Harvest | |
|---|---|---|---|---|---|---|
| | AF[1] | BA[2] | AF | BA | AF | BA |
| Untreated | 40 | ND[3] | 100 | ND | 4,386 | 255 |
| Ongoing | 403 | 3,597 | 150 | 3,000 | 385 | 4,785 |
| High Inoculum (M52) | ND | 21,200 | ND | 34,000 | 500 | 25,300 |
| Low Inoculum (M52) | ND | 3,800 | ND | 3,550 | 3,470 | 5,400 |

[1]Wild strains of aflatoxin-producing *A. flavus/parasiticus*.
[2]Biocompetitive agent. For the untreated soil and ongoing study, this is the parent NRRL 18991 strain. For the high and low inoculum treatments, this is the M52 mutant strain.
[3]No CFU detected.

In the low and high inoculum treatments with the M52 mutant, much better control of wild *A. flavus/-parasiticus* populations was achieved with the high inoculum treatment. This provides an indication that the amount of inoculum is an important consideration in achieving control through biological competition.

Results of aflatoxin analyses for the third crop growing season studies are presented in Table 5. A reduction in aflatoxin concentrations was again seen in peanuts grown in soils treated with a biocompetitive agent. Significantly, the greatest effect was seen in the edible peanuts. The 40 ppb found in all edible peanuts from soil last treated in the first crop growing season, which was a significant increase from the 1 ppb found in the second crop growing season, indicated that the biocompetitive agent may have been losing its effectiveness after being in the soil for three crop growing seasons. Over a tenfold reduction in aflatoxin was found in edible peanuts grown in soil treated with the high inoculum level of the M52 mutant compared to untreated soil (17 vs. 241 ppb).

TABLE 5

Third crop growing season aflatoxin concentrations (ppb) in peanuts from untreated soil, soil treated with a biocompetitive agent in the first crop growing season, (ongoing), and soil treated with high and low inoculum levels of the M52 mutant.

| Treatment | Jumbo | Medium | No. 1 | Edible Weighted Avg. | Other Edible | Oil Stock | Damage | Inedible Weighted Avg. |
|---|---|---|---|---|---|---|---|---|
| Untreated | 232 | 132 | 393 | 241 | 474 | 3,774 | 107,158 | 26,876 |
| Ongoing | 92 | 10 | 74 | 40 | 255 | 1,170 | 28,527 | 7,588 |
| High inoculum | 6 | 22 | 15 | 17 | 179 | 90 | 6,786 | 2,022 |
| Low inoculum | 8 | 25 | 38 | 29 | 302 | 40 | 21,875 | 7,071 |

Soil treated with the low inoculum level of the M52 mutant also resulted in a lower aflatoxin concentration in edible peanuts (29 ppb). The results from these treatments with the M52 mutant are more nearly like those seen from the 37 and 44 stress day samplings taken in the first crop growing season , and coupled with the results from the second crop growing season may indicate that maximum control is achieved in the crop growing season following inoculation.

There has been provided in accordance with the present invention, a biocontrol agent, compositions, and methods for the prevention and/or control of aflatoxin contamination in agricultural commodities. It can be seen from the preferred embodiments that many variations and alternatives may be practiced without departing from the spirit and scope of the invention. It is intended that the scope of this invention includes such variations and alternatives.

It is envisioned that any system for biocontrol delivery, known to the skilled artisan, can be used for the administration of non-aflatoxigenic *A. parasiticus* strains to agricultural crops of the soil in which they are grown. Additionally, carrier agents for biocontrol can be inert compounds or compositions including stabilizers and preservatives known in the art.

We claim:

1. A method of protecting peanuts susceptible to growth of an aflatoxin-producing fungus against contamination by aflatoxin comprising applying to the soil where the peanuts are grown a non-aflatoxigenic strain of *Aspergillus parasiticus* in an amount effective to inhibit growth of native *Aspergillus parasiticus* strains and their subsequent biosynthesis of aflatoxin.

2. A method of claim 1 wherein said non-aflatoxigenic strain of *Aspergillus parasiticus* possesses all of the identifying characteristics of ARS Culture Collection Number NRRL 18786 or NRRL 18991.

3. A method of claim 1 wherein the non-aflatoxigenic strain of *Aspergillus parasiticus* does not produce a detectable amount of dihydrobisfuran-containing intermediate in the aflatoxin biosynthetic pathway.

4. The method of claim 3 wherein said non-aflatoxigenic strain of *Aspergillus parasiticus* possesses all of the identifying characteristics of NRRL 18786.

5. A biocontrol composition for the amelioration of aflatoxin contamination in peanuts comprising a strain of *Aspergillus parasiticus* having all of the identifying characteristics of NRRL 18786 or NRRL 18991 and a carrier.

* * * * *